United States Patent
Ano et al.

(10) Patent No.: US 10,487,306 B2
(45) Date of Patent: Nov. 26, 2019

(54) **CULTURING METHOD FOR BACTERIA BELONGING TO GENUS *COLLIMONAS* AND STORAGE METHOD**

(71) Applicants: NEW ENVIRONMENTAL TECHNOLOGY COUNCIL, Chiyoda-ku, Tokyo (JP); KINKI UNIVERSITY, Higashiosaka-shi, Osaka (JP)

(72) Inventors: Takashi Ano, Kinokawa (JP); Toichiro Hirose, Tokyo (JP)

(73) Assignees: New Environmental Technology Council, Chiyoda-ku, Tokyo (JP); Kinki University, Higashiosaka-shi, Osaka (JP)

( * ) Notice: Subject to any disclaimer, the term of this patent is extended or adjusted under 35 U.S.C. 154(b) by 0 days.

(21) Appl. No.: 16/213,639

(22) Filed: Dec. 7, 2018

(65) Prior Publication Data

US 2019/0177682 A1    Jun. 13, 2019

Related U.S. Application Data

(62) Division of application No. 14/916,255, filed as application No. PCT/JP2013/073781 on Sep. 4, 2013, now abandoned.

(51) Int. Cl.
    *C12N 1/20*    (2006.01)
    *A01N 63/00*   (2006.01)
    *C12N 1/04*    (2006.01)

(52) U.S. Cl.
    CPC ............... *C12N 1/20* (2013.01); *A01N 63/00* (2013.01); *C12N 1/04* (2013.01)

(58) Field of Classification Search
    None
    See application file for complete search history.

(56) References Cited

FOREIGN PATENT DOCUMENTS

| JP | 10-243781 A | 9/1998 |
|---|---|---|
| JP | 2000-229802 A | 8/2000 |
| WO | WO 2013/038542 A1 | 3/2013 |
| WO | WO 2013/038575 A1 | 3/2013 |

OTHER PUBLICATIONS

International Search Report (PCT/ISA/210) dated Dec. 10, 2013, by the Japanese Patent Office as the International Searching Authority for International Application No. PCT/JP2013/073781.
Senechkin et al., Interaction of *Collirnonas* strain IS343 with *Rhizoctonia solani* at low carbon availability in vitro and in soil, Eur J Plant Pathol, 136(4): 789-802, 2013.
Sugai et al., The Abilities of Hinai-Green Tuff to Adjust pH and Activate Microorganisms, Shigen to Sozai, 121(10, 11): 513-520, 2005.
De Boer et al., *Collimonas fungivorans* gen. nov., sp. Nov., a chitinolytic soil bacterium with the ability to grow on living fungal hyphae, International Journal of Systematic and Evolutionary Microbiology, 54:857-864, 2004.
Oxoid Manual, 1982., Oxoid Limited, pp. 314-315.
Takazaki, Green-tuff landslide areas are beneficial for rice nutrition in Japan, Annals of the Brazilian Academy of Sciences, 78:749-763, 2006.

*Primary Examiner* — Thane Underdahl
(74) *Attorney, Agent, or Firm* — Buchanan Ingersoll & Rooney PC

(57) ABSTRACT

Provided are a novel cultivation method and a storage method that are suitable for storing bacteria belonging to the genus *Collimonas* for a long period of time. The cultivation method for bacteria belonging to the genus *Collimonas* is characterized in that bacteria belonging to the genus *Collimonas* are cultivated in a sealed state on a culture medium that includes a rice bran culture medium and/or a soy pulp culture medium. The storage method for bacteria belonging to the genus *Collimonas* is characterized in that the cultivated bacteria belonging to the genus *Collimonas* are stored at room temperature.

2 Claims, 6 Drawing Sheets

(a)

(b)

(c)

(a)

(b)

(c)

(a)

(b)

(c)

US 10,487,306 B2

CULTURING METHOD FOR BACTERIA BELONGING TO GENUS *COLLIMONAS* AND STORAGE METHOD

CROSS REFERENCE TO RELATED APPLICATIONS

This application is a Divisional of application Ser. No. 14/916,255, filed Mar. 3, 2016, which is a 371 application of International Application No. PCT/JP2013/073781, filed Sep. 4, 2013, the contents of which are hereby expressly incorporated by reference in their entirety for all purposes.

TECHNICAL FIELD

This invention relates to a method for culturing microorganisms, and specifically relates to a culturing method that is suitable for the storage of bacteria belonging to the genus *Collimonas* for a long period of time.

BACKGROUND ART

Bacteria belonging to the genus *Collimonas* are known as microorganisms that suppress the proliferation of plant pathogenic bacteria, on which various studies are conducted. If the action of bacteria belonging to the genus *Collimonas* to suppress the proliferation of plant pathogenic bacteria is revealed, then practical use of these bacteria in microorganism agrochemicals can be expected.

Microorganisms that are incorporated in microorganism agrochemicals are desired to have high storage stability so as to exert the actions possessed by the respective microorganisms.

As the storage of microorganisms, a freeze storage-drying method, a storage method utilizing a freeze storage-drying method suggested in Patent Literature 1, and the like are known.

CITATION LIST

Patent Literature

Patent Literature 1: JP H10-243781 A

SUMMARY OF INVENTION

Technical Problem

The inventors conducted intensive studies so as to obtain a method for storing microorganisms which enables storage for a long period of time other than the above-mentioned conventionally-known methods for storing microorganisms.

Consequently, the inventors succeeded in storing bacteria belonging to the genus *Collimonas* for about one year by adding Towada stone, which is green tuff, as an additive, under certain conditions of a culture medium, or after pre-culturing.

Therefore, this invention aims at providing novel culturing and storage methods that are suitable for storing bacteria belonging to the genus *Collimonas* for a long period of time.

Solution to Problem

In order to solve the above-mentioned problem, the following inventions are suggested.

The invention of claim 1 is a method for culturing bacteria belonging to the genus *Collimonas*, including culturing the bacteria belonging to the genus *Collimonas* in a culture medium containing a rice bran culture medium and/or a soy pulp culture medium in a sealed state.

The invention of claim 2 is the method for culturing bacteria belonging to the genus *Collimonas* according to claim 1, wherein green tuff is added as an additive to the culture medium containing a rice bran culture medium and/or a soy pulp culture medium.

Advantageous Effects of Invention

According to this invention, novel culturing and storage methods that are suitable for storing bacteria belonging to the genus *Collimonas* for a long period of time can be provided.

DESCRIPTION OF EMBODIMENTS

Figure 1:
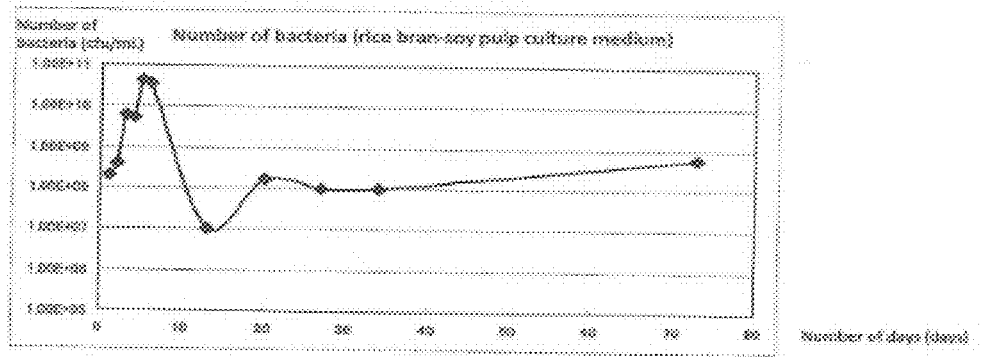
FIG. 1 (*a*) is a drawing illustrating the result of the count of the number of the viable bacteria of D-25 strain in a rice bran-soy pulp culture medium, FIG. 1 (*b*) is a drawing illustrating the result of the count of the number of the viable bacteria of D-25 strain in a soy pulp culture medium, and FIG. 1 (*c*) is a drawing illustrating the result of the count of the number of the viable bacteria of D-25 strain in a rice bran culture medium.
Figure 1:
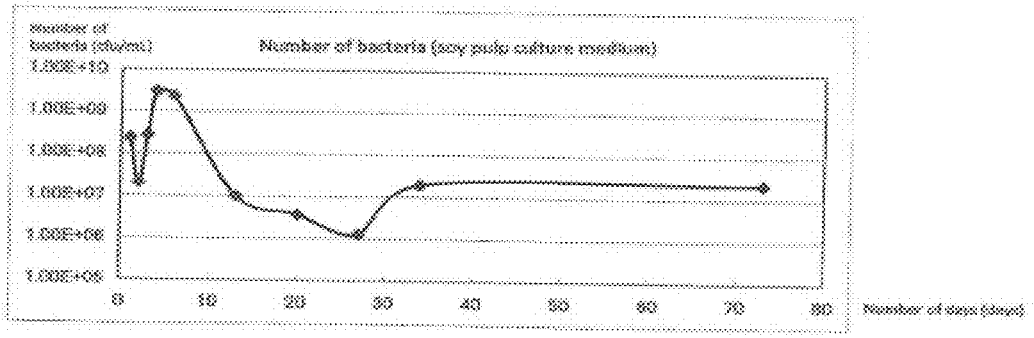
Figure 1:
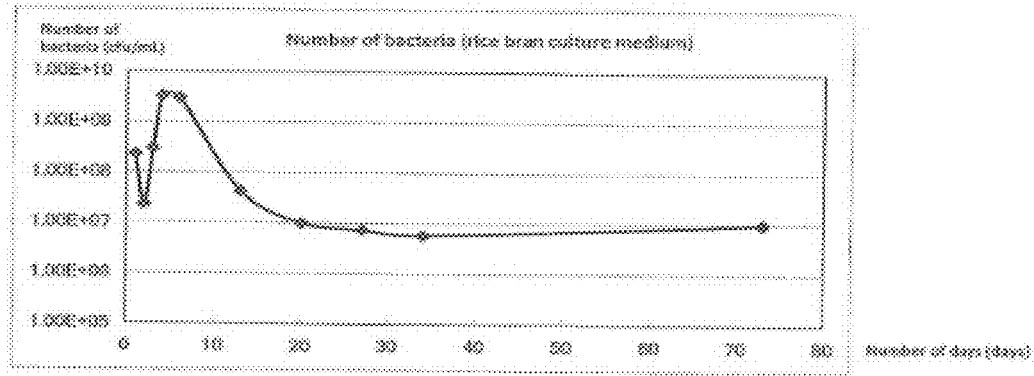

Hereinafter the exemplary embodiment of the present invention will be explained.

The microorganisms used in the exemplary embodiments were microorganisms belonging to the *Collimonas* sp. Examples of the microorganisms belonging to the *Collimonas* sp. include D-25 strain, Cal2 strain and Cal31 strain. Among these, the mycological properties of D-25 strain are as shown in Tables 1 to 3.

TABLE 1

Results of physiological and biochemical tests on D-25 strain (form, motility, growth temperature tests, etc.)

| Test item | | Test result |
|---|---|---|
| Culture temperature | | 25° C. |
| Cell form | | Bacillus, extended type is present (0.9-1.0 × 2.0-4.0 μm) |
| Gram stainability | | − |
| Presence or absence of spore | | − |
| Motility | | − |
| Colony form | | Culture medium: R2A agar |
| | | Culture time: 48 hours |
| | | Diameter: 2.0-3.0 mm |
| | | Color tone: pale yellow |
| | | Shape: circular shape |
| | | State of projection: lens-shape |
| | | Periphery: wave shape |
| | | Shape of surface, and the like: smooth |
| | | Transparency: translucent. |
| | | Viscosity: viscous |
| Growth temperature test | 30° C. | + |
| | 37° C. | − |
| Catalase reaction | | + |
| Oxidase reaction | | + |
| Generation of acid/gas from glucose | | −/− |
| O/F test (oxidation/fermentation) | | −/− |
| Growth under anaerobic condition | | − |

+: positive,
−: negative

TABLE 2

Results of physiological and biochemical tests on D-25 strain (biochemical tests, assimilation tests)

| Test item | Judgment | Test item | Judgment |
|---|---|---|---|
| Nitrate reduction* | − | D-mannitol** | + |
| Indole production* | − | N-Acetyl-D-glucosamine** | + |
| Glucose acidification* | − | Maltose** | − |
| Arginine dihydrolase* | − | Potassium gluconate** | + |
| Urease* | − | n-Capric acid** | − |
| Esculin hydrolysis* | − | Adipic acid** | − |
| Gelatin hydrolysis* | − | dl-Malic acid** | + |

TABLE 2-continued

Results of physiological and biochemical tests on D-25 strain (biochemical tests, assimilation tests)

| Test item | Judgment | Test item | Judgment |
|---|---|---|---|
| β-Galactosidase* | − | Sodium citrate** | + |
| Glucose** | + | Phenyl acetate** | − |
| L-Arabinose** | + | Cytochrome oxidase* | − |
| D-Mannose** | + | | |

*biochemical test,
**assimilation test
+: positive,
−: negative

TABLE 3

Results of physiological and biochemical tests on D-25 strain (enzyme reaction tests)

| Test item | Test result |
|---|---|
| Alkali phosphatase | + |
| Esterase (C4) | + |
| Esterase lipase (C8) | + |
| Lipase (C14) | + |
| Leucine allylamidase | + |
| Valine allylamidase | − |
| Cystine allylamidase | − |
| Trypsin | − |
| Chymotrypsin | − |
| Acidic phosphatese | + |
| Naphthol-AS-B1-phosphohydrolase | + |
| α-Galactosidase | − |
| β-Galactosidase | + |
| β-Glucuronidase | − |
| α-Glucosidase | − |
| β-Glucosidase | − |
| N-Acetyl-β-glucosaminidase | − |
| α-Mannosidase | − |
| α-Fucosidase | − |

+: positive,
−: negative

D-25 strain, which has the mycological properties described in Tables 1 to 3, was assumed to be relegated to the *Collimonas* taxon. This strain was deposited with the accession number NITE P-1104 with the Patent Microorganisms Depositary of the National Institute of Technology and Evaluation (2-5-8, Kazusakamatari, Kisarazu-shi, Chiba, Japan) on Jun. 9, 2011.

Towada stone as the additive used in this exemplary embodiment is green tuff that is mined in Hinaimachi, Odate-shi, Akita, Japan, has a formal nomenclature "quartz dacitic pumiceous tuff", and is known under the name of "green tuff".

Towada stone is characterized by being a composite ore having a mineral composition containing quartz, albite, chlorite and the like as mineral composition, and much minerals. Furthermore, since Towada stone is porous, and thus has actions to adsorb and release substances, and the like, it is also utilized as an agricultural fertilizer. The major composition of Towada stone is shown in Table 4.

TABLE 4

| SiO$_2$ Silicon oxide | Al$_2$O$_5$ Aluminum oxide | Fe$_2$O$_3$ Iron oxide | TiO$_2$ Titanium oxide | CaO Calcium oxide | MgO Magnesium oxide | Na$_2$O Sodium oxide | K$_2$O Potassium oxide |
|---|---|---|---|---|---|---|---|
| 72.1 | 12.7 | 3.2 | 0.5 | 1.3 | 1.0 | 4.1 | 2.3 |

Example 1

Storage of *Collimonas* sp. D-25 strain (hereinafter referred to as "D-25 strain") was tried in a rice bran-soy pulp culture medium and a R2A culture medium of D-25 strain by adding glycerin and Towada stone.

The culture medium in the pre-culturing was used as an R2A culture medium. The culture media in the main culturing were used as a rice bran-soy pulp culture medium and an R2A culture medium. Glycerin and Towada stone were used as the additive materials for the culture media in the main culturing. The composition of the R2A culture medium is as follows.

(R2A culture medium composition (contents per 1 L))
Pepton: 0.5 g
Yeast extract: 0.5 g
Casamino acid: 0.5 g
Glucose: 0.5 g
Soluble starch: 0.5 g
Sodium pyruvate: 0.5 g
K$_2$HPO$_4$: 0.3 g
MgSO$_4$: 0.05 g Experimental Method D-25 strain was inoculated into 2 mL of an R2A culture medium with a pick, pre-cultured for 2 days, at 24° C. at 200 rpm, and the number of the viable bacteria was counted.

After the pre-culturing, 2% of D-25 strain was inoculated into 10 mL of an R2A culture medium, and 10 mL of a rice bran-soy pulp culture medium (rice bran and soy pulp: each 1% (w/v)), respectively, and the culture media were subjected to main culturing for 6 days, at 24° C. at 200 rpm.

1,000 μL of each of the bacteria liquids of the R2A culture medium and the rice bran-soy pulp culture medium on day 6 of the culturing was dispensed into a 1.5 mL sample tube, centrifuged at 5,000 rpm for 3 minutes, and the supernatant was discarded, whereby a fungus body was obtained.

Four pieces of sample tubes containing only each fungus body were prepared, and aqueous solutions containing glycerin at concentrations of 0% (only sterilized distilled water), 10% (W/W), 30% (W/W) and 50% (W/W), each 1 mL, were added to the respective four sample tubes, and the sample tubes were sealed with paraffin films and allowed to stand still at 24° C.

Furthermore, fungus bodies from the respective bacteria liquids of the above-mentioned R2A culture medium and the rice bran-soy pulp culture medium on day 6 of the culturing were obtained. Two pieces of sample tubes containing each fungus body alone were separately prepared, and 200 μL of sterilized water was added to the respective two sample tubes, sterilized Towada stone was further added by 0.5 g and 1.0 g, respectively, the sample tubes were thoroughly subjected to vortex, the openings were thoroughly wrapped with paraffin films, and the sample tubes were allowed to stand still at 24° C.

For the samples that had undergone the main culturing in the above-mentioned R2A culture medium and rice bran-soy pulp culture medium, the number of the viable bacteria was counted on day 0, day 2, day 4 and day 6. For the samples to which the above-mentioned glycerin had been added, the number of the viable bacteria was counted on day 3 and day 6. For the samples to which the above-mentioned Towada stone had been added, the number of the viable bacteria was counted on day 6.

(Results)

For the D-25 strain that had been pre-cultured in the R2A culture medium, the number of the viable bacteria on day 2 of the culturing was 5.67×10$^9$ cfu/ml. Tables 5 to 7 respectively show the results of the count of the number of the viable bacteria of the D-25 strain in the above-mentioned samples that had undergone the main culturing in the R2A culture medium and the rice bran-soy pulp culture medium, the sample to which the above-mentioned glycerin had been added, and the sample to which the above-mentioned Towada stone had been added.

TABLE 5

Results of count of number of viable bacteria of D-25 strain in samples that had undergone main culturing in R2A culture medium and rice bran-soy pulp culture medium

| | Number of viable bacteria (cfu/ml) | |
|---|---|---|
| Days after culturing | Rice bran-soy pulp culture medium | R2A culture medium |
| Day 0 | 7.67 × 10$^7$ | 8.00 × 10$^7$ |
| Day 2 | 1.30 × 10$^{10}$ | 3.34 × 10$^9$ |
| Day 4 | 1.23 × 10$^{10}$ | 1.26 × 10$^9$ |
| Day 6 | 1.20 × 10$^{10}$ | 6.67 × 10$^8$ |

TABLE 6

Results of count of number of viable bacteria of D-25 strain in samples to which glycerin had been added

| | Number of viable bacteria (cfu/ml) | | | |
|---|---|---|---|---|
| | Rice bran-soy pulp culture medium | | R2A culture medium | |
| Concentration of addition of glycerin | Day 3 after addition | Day 6 after addition | Day 3 after addition | Day 6 after addition |
| 0% | 1.10 × 10$^9$ | 9.00 × 10$^8$ | 4.67 × 10$^8$ | 3.67 × 10$^8$ |
| 10% | 2.00 × 10$^7$ | 1.03 × 10$^8$ | 4.00 × 10$^8$ | 1.20 × 10$^8$ |
| 30% | 1.53 × 10$^7$ | 4.00 × 10$^8$ | 9.33 × 10$^5$ | 1.67 × 10$^4$ |
| 50% | 1.10 × 10$^5$ | N.D. | N.D. | N.D. |

TABLE 7

Results of count of number of viable bacteria of D-25
strain in samples to which Towada stone had been added

| | Number of viable bacteria (cfu/ml) | |
|---|---|---|
| Additives | Rice bran-soy pulp culture medium Day 6 after addition | R2A culture medium Day 6 after addition |
| 200 µL of Sterilized water 0.5 g of Towada stone | $3.00 \times 10^8$ | $1.53 \times 10^8$ |
| 200 µL of Sterilized water 1.0 g of Towada stone | $7.30 \times 10^8$ | $8.00 \times 10^8$ |

(Consideration)

When the samples in which D-25 strain was cultured in a rice bran-soy pulp culture medium and an R2A culture medium are compared, the rice bran-soy pulp culture medium showed more excellent proliferation property as a whole, and the number of the viable bacteria was able to be retained for a long time period (Table 5). Furthermore, $10^8$ cfu/ml was maintained under an ordinary temperature even after 8 months had passed. The reason therefor is considered that, since the culture medium components were carried into at large amounts in the centrifugation of the rice bran-soy pulp culture medium (a part of the rice bran and the soy pulp precipitates as a precipitation), the number of the viable bacteria was able to be maintained for a long time.

Bacteria belonging to the genus *Collimonas* are known as microorganisms that proliferate under a poor nutrition environment, for example, microorganisms that proliferate in an R2A culture medium, but are difficult to proliferate in a culture medium containing much nutrient contents. Furthermore, regarding the storage of the bacteria, it is known that the bacteria are stored at a low temperature of 4° C. or less.

From the results of the count of the number of the viable bacteria in the above-mentioned D-25 strain, it was confirmed that the bacteria proliferate also in the rice bran-soy pulp culture medium, which contains more nutrient contents than that of the above-mentioned R2A culture medium, and it can also be confirmed that the number of the viable bacteria can be maintained under an ordinary temperature over 8 months under a sealed condition.

Furthermore, it is considered that, if sterilized Towada stone is added to a sealable container, D-25 strain is added thereto and then a small amount of water is added thereto, the bacteria can be stored in a powdery form judging from appearance (Table 7). This method can prevent the death of fungus bodies due to vacuum drying and lyophilization.

Example 2

The storage of D-25 strain in a rice bran culture medium or a soy pulp culture medium, or in a rice bran-soy pulp culture medium was tried. The culture medium in the pre-culturing was the same as the R2A culture medium described in Example 1.

Experimental Method

D-25 strain was inoculated into 2 mL of a R2A culture medium with a pick, pre-cultured for 2 days, at 24° C. at 200 rpm, and the culture liquid was centrifuged at 6,000 rpm for 3 minutes, the supernatant was removed, an equivalent amount of saline was added thereto, and this was used as a bacteria liquid for inoculation.

A soy pulp-rice bran culture medium (each 1% (w/v)), a soy pulp culture medium (1% (w/v)) and a rice bran culture medium (1% (w/v)), each 100 mL, were prepared in flasks, and inoculation was conducted by adding 100 µL of the bacteria liquid prepared above. After the inoculation, the culture media were cultured under shaking for 6 days at 24° C. and 200 rpm, and the numbers of the viable bacteria were counted.

Thereafter, each culture liquid was transferred from the flask to a bottle, and static culturing was conducted. The number of the viable bacteria was counted every week in the first four weeks, thereafter the number of the viable bacteria was counted every month. The results of the count of the numbers of the viable bacteria of D-25 strain in the above-mentioned three kinds of culture liquids are shown in FIG. 1.

(Results and consideration)

In the soy pulp-rice bran culture medium, the bacteria proliferated to $10^{10}$ cfu/ml on day 6 (FIG. 1 (*a*)), and the bacteria proliferated to $10^9$ cfu/ml in the soy pulp culture medium and the rice bran culture medium, respectively (FIGS. 1 (*b*) and (*c*)).

At after 1 week from the transfer to the bottle, the bacteria decreased by $10^2$ cfu/ml in each culture medium (FIG. 1). It is considered to be attributed to air blockage and the static culturing.

After transferred to the bottle, the number of the viable bacteria became 10 times in 2 weeks, and was retained at $10^8$ cfu/ml for another two months, in the soy pulp-rice bran culture medium (FIG. 1 (*a*)).

In the soy pulp culture medium, the number of the viable bacteria became ⅒ in 2 weeks, and increased to 10 times again in 3 weeks. Thereafter the number was retained at $10^7$ cfu/ml (FIG. 1 (*b*)).

In the rice bran culture medium, the number of the viable bacteria decreased to ⅒ in 3 weeks, and was retained at $10^6$ cfu/ml thereafter.

It was confirmed also in this Example that D-25 strain proliferates in rice bran and soy pulp culture media, and that the number of the viable bacteria is retained at a predetermined number.

Example 3

The storage of respective strains: D-25 strain, *Collimonas* sp Cal2 strain (hereinafter referred to as "Cal2 strain") and *Collimonas* sp. Cal31 strain (hereinafter referred to as "Cal31 strain") in a rice bran-soy pulp culture medium was tried. The culture medium in the pre-culturing was the same as the R2A culture medium described in Example 1.

Experimental Method

The D-25 strain, Cal2 strain and Cal31 strain that had been stored in the R2A culture medium at 4° C. were each inoculated in a new R2A liquid culture medium, and pre-cultured at 24° C. for 2 days.

After the pre-culturing, 20 mL of a culture medium to which rice bran and soy pulp had been added by each 1% was prepared, and 200 µL of the pre-culture liquid was inoculated (1% inoculation). After the inoculation, culturing was conducted under shaking at 24° C. for 3 days at 120 rpm.

After the culturing, the numbers of the viable bacteria were counted for Cal2 strain and Cal31 strain, and whether or not these strains show similar growth to that of D-25 strain was confirmed.

(Results)

For the Cal2 strain, Cal31 strain and D-25 strain pre-cultured in the R2A culture medium, the numbers of the viable bacteria after the pre-culturing were respectively as follows.

D-25 strain: $4.3 \times 10^9$ cfu/mL
Cal2 strain: $1.8 \times 10^9$ cfu/mL
Cal31 strain: $5.3 \times 10^9$ cfu/mL Table 8 shows the result of the count of the numbers of the viable bacteria for the Cal2 strain, Cal31 strain and D-25 strain.

TABLE 8

| | Number of the viable bacteria (cfu/ml) | | |
|---|---|---|---|
| | D-25 strain | Cal2 strain | Cal31 strain |
| At inoculation | $2.8 \times 10^7$ | $8.8 \times 10^6$ | $4.1 \times 10^7$ |
| On day 3 after inoculation | $7.6 \times 10^9$ | $1.6 \times 10^9$ | $3.3 \times 10^9$ |

For the Cal2 strain and Cal31 strain, it was found that both of these strains grow up to $10^9$ cfu/ml when cultured in a rice bran-soy pulp culture medium for 3 days. The D-25 strain showed a slightly higher number of the viable bacteria than those of the Cal2 strain and Cal31 strain.

It was suggested by this Example that strains belonging to the genus Collimonas (Collimonas sp.) proliferate in rice bran and soy pulp culture media, and that a predetermined number of viable bacteria can be retained.

Reference Example 1

<Preparation of Microorganism Formulation Using D-25 Strain>

Using the culture liquid of D-25 strain, which was cultured in a rice bran-soy pulp culture medium in Example 3, an experiment for preparing a microorganism formulation was conducted.

As a support for fixing D-25 strain, Towada stone, which had been processed into a powdery form, was used.

Experimental Method

The culture liquid of D-25 strain by a rice bran-soy pulp culture medium prepared in Example 3 was dispensed into a 2 mL centrifuge tube (15 mL volume). The number of the viable bacteria was $1.5 \times 10^{10}$ cfu/2 mL.

A Towada stone powder that had undergone a dry heat sterilization treatment was prepared, 5 g of which was added to the above-mentioned centrifuge tube including the culture liquid of D-25 strain, and the mixture was stirred by a Mothers small reactor. The stirring was conducted three times in total, for 1 minute respectively, with changing the upper and lower attachment positions. During the stirring, some agglomerates with large particle sizes of Towada stone were produced, and were processed by crushing with a platinum loop.

0.2 g of the prepared formulation was weighed, and 1 mL of sterilized water was added thereto, and the number of the viable bacteria of D-25 strain was counted by using this.
(Results)

The number of the viable bacteria of the D-25 strain to which Towada stone was added was $5.5 \times 10^7$ cfu/g, and thus a microorganism formulation of about $10^7$ cfu/g was to be prepared. The factor of the decrease in the number of the viable bacteria includes too vigorous stirring. However, since Collimonas sp. can ensure a large amount of bacteria within a short time, it is considered that this decrease can be covered by increasing the initial injection amount.

Example 4

In Example 1, it was considered that it is possible to store D-25 strain in a powdery form by adding Towada stone to a culture liquid of D-25 strain. Therefore, in this Example, the content of the Towada stone powder and the water content suitable for the growth of bacteria belonging to the genus Collimonas were considered.

The bacteria belonging to the genus Collimonas used in this Example was used as D-25 strain. As a support for fixing D-25 strain, Towada stone was used, which had been processed into a powdery form of from 1 μm to 80 μm.

Experimental Method

The Towada stone powder was weighed 0.9 g, 0.7 g and 0.5 g, and each was dispensed in a test tube, and subjected to a sterilization treatment in a dry heat sterilizer.

Figure 2:
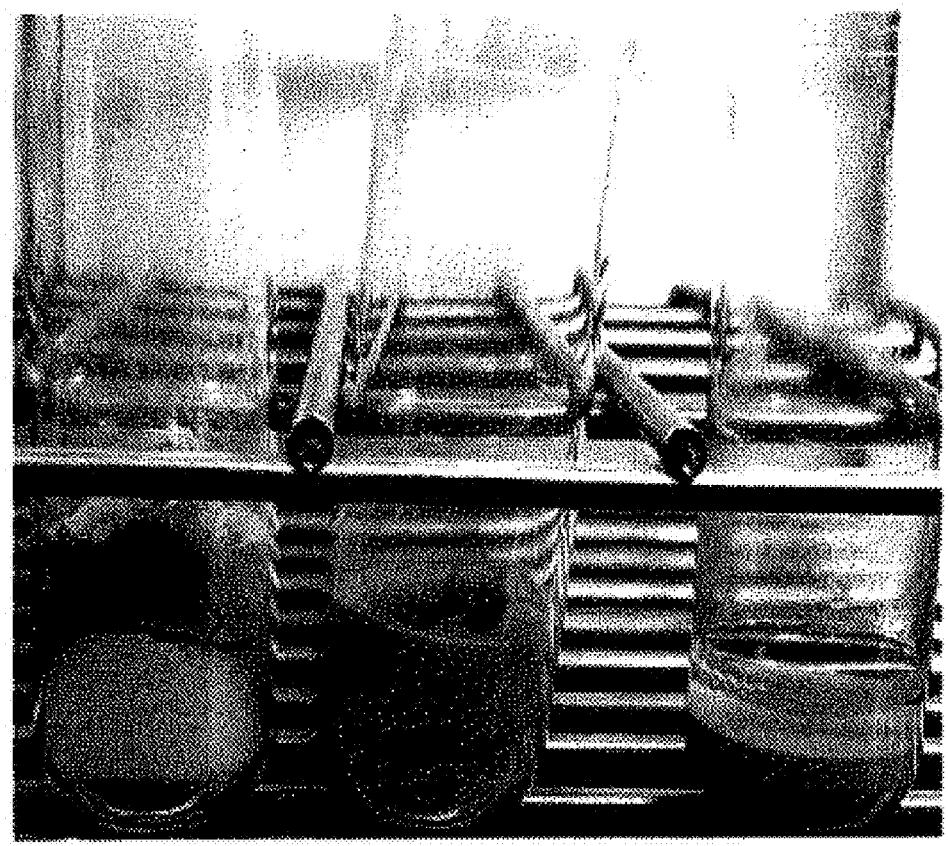
FIG. 2 shows the state in which D-25 strain was inoculated in a Towada stone powder. From the left, 0.9 g of a Towada stone powder to which 100 µL of a bacteria liquid of D-25 strain was inoculated, 0.7 g of a Towada stone powder to which 100 µL of a bacteria liquid of D-25 strain was inoculated and 200 µL of sterilized water was added, and a 0.5 g Towada stone powder to which 100 µL of a bacteria liquid of D-25 strain was inoculated and 400 µL of sterilized water was added.

A pre-culture liquid of Collimonas D-25, which had been inoculated from an R2A culture medium to a 1/10 TSB culture medium in advance and pre-cultured, was prepared, and 0.9 g of a Towada stone powder to which 100 μL of the above-mentioned pre-culture liquid had been inoculated (Sample 1), 0.7 g of a Towada stone powder to which 100 μL of the above-mentioned pre-culture liquid had been inoculated and 200 μL of sterilized water had been added (Sample 2), and 0.5 g of a Towada stone powder to which 100 μL of the above-mentioned pre-culture liquid had been inoculated and 400 μL of sterilized water had been added (Sample 3) were prepared. After the inoculation, culturing was conducted at room temperature. The states of the culturing are shown in FIG. 2. The number of the viable bacteria of the pre-cultured D-25 strain was $7.0 \times 10^5$ cfu/mL.

After 4 days of culturing, in order to measure the number of the viable bacteria, 3 mL of sterilized water was added to each sample, and the sample was stirred by vortex for 30 seconds. After the stirring, the sample was allowed to stand still for 10 minutes to precipitate the Towada stone powder, and the number of the viable bacteria of D-25 strain was counted by using the supernatant.
(Results)

Figure 3:
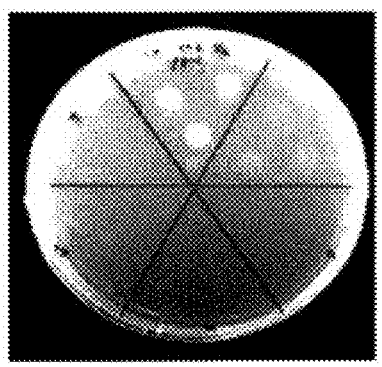
FIG. 3 is a drawing showing the growth states of the D-25 strain at after 4 days of culturing from the states illustrated in FIG. 2, in which FIG. 3 (*a*) shows 0.9 g of a Towada stone powder to which 100 µL of a bacteria liquid of D-25 strain was inoculated, FIG. 3 (*b*) shows 0.7 g of a Towada stone powder to which 100 µL of a bacteria liquid of D-25 strain was inoculated and 200 µL of sterilized water was added, and FIG. 3 (*c*) shows a 0.5 g Towada stone powder to which 100 µL of a bacteria liquid of D-25 strain was inoculated and 400 µL of sterilized water was added.
Figure 3:
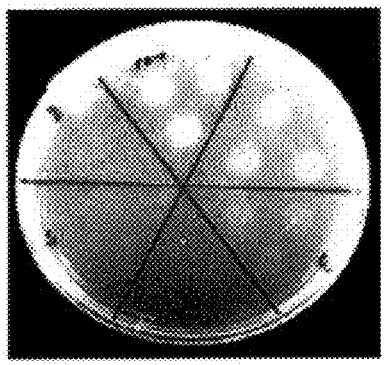
Figure 3:
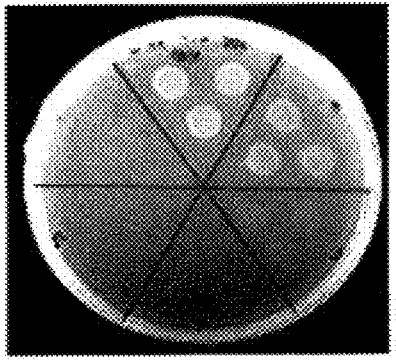

Table 9 shows the results of the count of the numbers of the viable bacteria of D-25 strain. The numbers of the viable bacteria are represented by the values when 3 mL of sterilized water was added. Furthermore, the states of the D-25 strain during the count are shown in FIG. 3.

TABLE 9

| | Sample 1 Towada stone powder D-25 strain bacterial liquid Sterilized water: none | Sample 2 Towada stone powder D-25 strain bacterial liquid Sterilized water | Sample 3 Towada stone powder D-25 strain bacterial liquid Sterilized water |
|---|---|---|---|
| Number of viable bacteria (cfu/mL) | No growth | $1.2 \times 10^7$ | $3.2 \times 10^7$ |

For Sample 1, the growth of D-25 strain was not seen. In FIG. 3 (a), the matters that look white seem to be the powder of Towada stone.

For Samples 2 and 3, the growth of D-25 strain was confirmed. Specifically, in Sample 3, viable bacteria were confirmed up to $10^4$ cfu/mL.

Example 5

In Example 4, when D-25 strain was inoculated into the Towada stone powder, and sterilized water was added, the growth of D-25 strain was able to be confirmed. Therefore, in this Example, an experiment for confirming a weight ratio of the Towada stone to the water content suitable for the growth of D-25 strain was conducted.

Experimental Method 1

Figure 4:
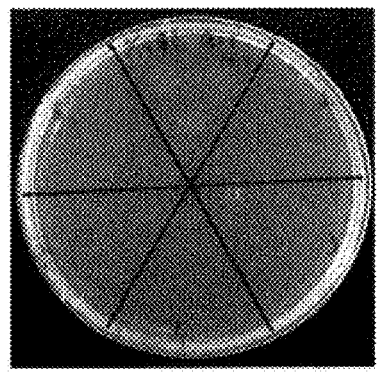
FIG. 4 is a drawing showing the growth states of D-25 strain after inoculating D-25 strain in culture media containing Towada stone and culturing, and subjecting the culture media to a vacuum drying treatment, in which FIG. 4 (*a*) shows 0.9 g of a Towada stone powder to which 100 µL of a bacteria liquid of D-25 strain was inoculated, FIG. 4 (*b*) shows 0.7 g of a Towada stone powder to which 100 µL of a bacteria liquid of D-25 strain was inoculated and 200 µL of sterilized water was added, and FIG. 4 (*c*) shows a 0.5 g Towada stone powder to which 100 µL of a bacteria liquid of D-25 strain was inoculated and 400 µL of sterilized water was added.
Figure 4:
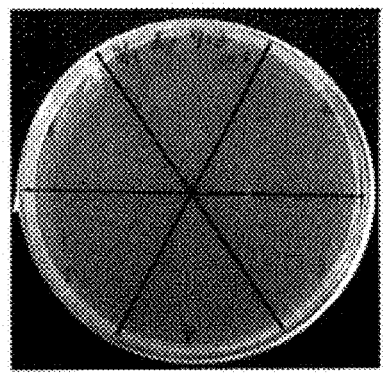
Figure 4:
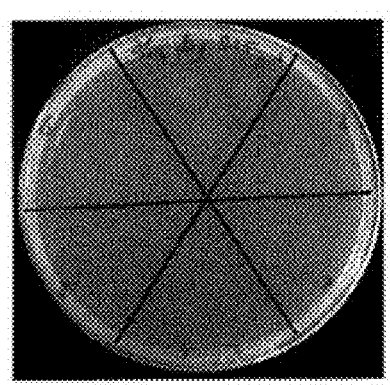

D-25 strain was cultured for a week in a culture medium containing Towada stone, and vacuum drying was conducted for three days (a reduced pressure treatment was conducted once, for about 30 seconds) to remove the water content. After the drying, 3 mL of sterilized water was added, the resultant was suspended, and the number of the viable bacteria in the suspension liquid was counted.
<Prepared Samples>
0.9 g of a Towada stone powder, to which 100 μL of the pre-culture liquid of D-25 strain was inoculated
0.7 g of a Towada stone powder, to which 100 μL of the pre-culture liquid of D-25 strain was inoculated, and 200 μL of sterilized water was added
0.5 g of a Towada stone powder, to which 100 μL of the pre-culture liquid of D-25 strain was inoculated, and 400 μL of sterilized water was added
(Results)
As a result of the count of the numbers of the viable bacteria, the growth of D-25 strain was not detected in any sample, unlike as indicated in FIG. 4. Thus, it is considered that the D-25 strain was killed.

Experimental Method 2

Figure 5:
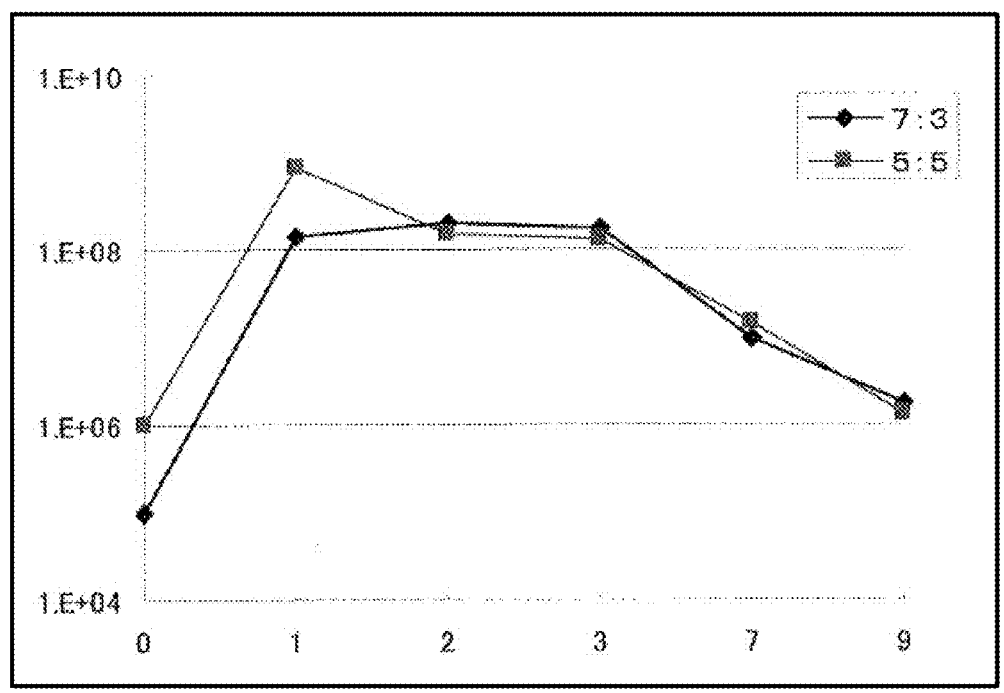
FIG. 5 is a graph in which samples in which the weight of Towada stone and the amount of the water content in the water content containing a pre-culture liquid of D-25 strain and sterilized water were preset to 7:3 and 5:5 were made, and the numbers of the viable bacteria in the respective D-25 strains were counted.
Figure 6:
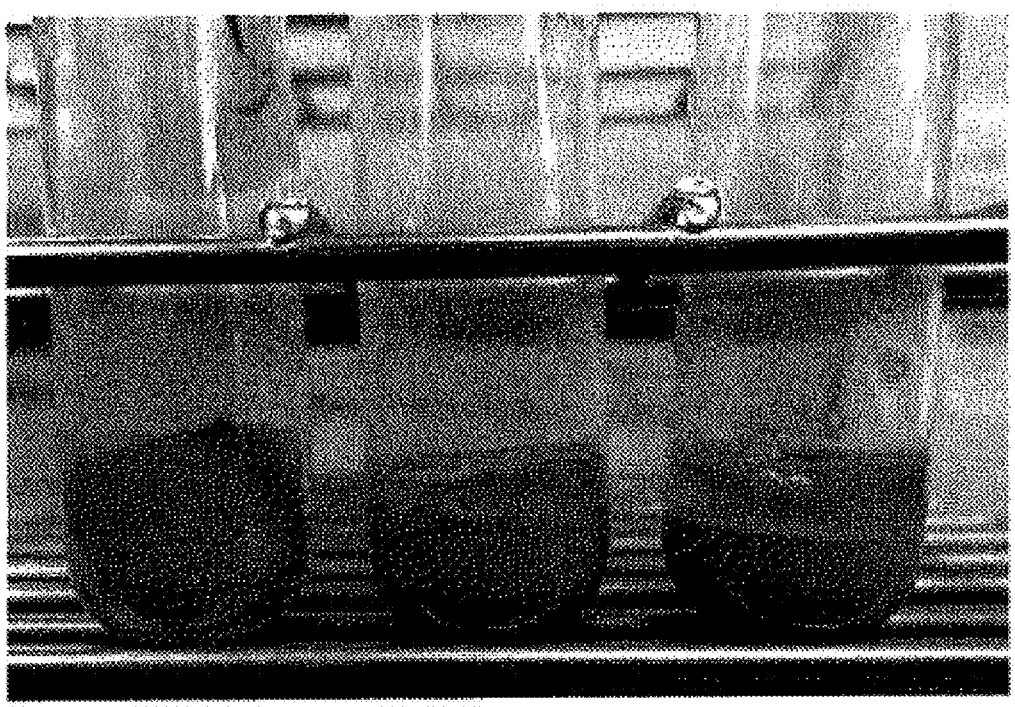
FIG. 6 shows the state in which D-25 strain was inoculated to a Towada stone powder. From the left, 0.7 g of a Towada stone powder to which 100 µL of a bacteria liquid of D-25 strain was inoculated and 200 µL of TSB and 3% of glycerin was added, 0.6 g of a Towada stone powder to which 100 μL of a bacteria liquid of D-25 strain was inoculated and 300 μL of TSB and 3% of glycerin was added, and 0.5 g of a Towada stone powder to which 100 μL of a bacteria liquid of D-25 strain was inoculated and 400 μL of TSB and 3% of glycerin was added.

Samples in which the ratio of the weight of Towada stone and the amount of the water content of the water content containing the pre-culture liquid of D-25 strain and sterilized water was adjusted to 7:3 and 5:5, respectively, were prepared, and the respective number of the viable bacteria of D-25 strain was counted.
(Results)
As illustrated in FIG. 5, survival for one week or more was observed, and thus it was confirmed that a number of the viable bacteria of about $10^6$ cfu/mL was retained.

Experimental Method 3

In the above-mentioned Experimental Method 1, since the *Collimonas* was killed when a vacuum drying treatment was conducted after the culturing of D-25 strain, TSB and 3% of glycerin were added instead of the sterilized water, and culturing was tried. In addition, the number of the viable bacteria of the pre-culture liquid of D-25 strain was $2.6 \times 10^7$ cfu/mL.
Culturing was conducted in the prepared sample for 4 days, 3 mL of sterilized water was added thereto to form a suspension liquid, and the number of the viable bacteria was counted.
<Prepared Samples>
Sample 1: 0.7 g of a Towada stone powder, to which 100 μL of a pre-culture liquid of D-25 strain was inoculated, and 200 μL of TSB and 3% of glycerin were added
(The ratio of the weight of the Towada stone to the amount of the water content of the water content containing the pre-culture liquid of D-25 strain was 7:3)
Sample 2: 0.6 g of a Towada stone powder, to which 100 μL of a pre-culture liquid of D-25 strain was inoculated, and 300 μL of TSB and 3% of glycerin were added
(The ratio of the weight of the Towada stone to the amount of the water content of the water content containing the pre-culture liquid of D-25 strain was 6:4)
Sample 3: 0.5 g of a Towada stone powder, to which 100 μL of a pre-culture liquid of D-25 strain was inoculated, and 400 μL of TSB and 3% of glycerin were added
(The ratio of the weight of the Towada stone to the amount of the water content of the water content containing the pre-culture liquid of D-25 strain was 5:5)
(Results)
The results of the count of the numbers of the viable bacteria are shown in Table 10.

TABLE 10

|  | Sample 1 | Sample 2 | Sample 3 |
| --- | --- | --- | --- |
| Number of viable bacteria (cfu/mL) | $2.1 \times 10^6$ | $1.3 \times 10^5$ | $1.2 \times 10^7$ |

As illustrated in FIG. 5, since a number of the viable bacteria of about $10^8$ cfu/mL was obtained in 0.5 g of the Towada stone powder, to which 100 μL of the pre-culture liquid of D-25 strain was inoculated and 400 μL of sterilized water was added, a result that is similar to this result was obtained in Sample 1 in this Example.

It was confirmed by this Example that D-25 strain can be cultured not only in Towada stone alone, but also in a TSB culture medium (slightly diluted by a bacteria liquid) with Towada stone.

Furthermore, it was suggested that, in the case when the ratio of the weight of the Towada stone to the amount of the water content of the water content containing the pre-culture liquid of D-25 strain is 7:3, the culturing of D-25 strain can be promoted, and thus it is possible to store for a long period of time.

Reference Example

In Examples 4 and 5, when D-25 strain was inoculated into the Towada stone powder and sterilized water was added, the growth of the D-25 strain was able to be confirmed. Therefore, as a reference example, an experiment to confirm the growth states of the D-25 strain with changing the conditions of the Towada stone powder and D-25 strain and to observe the suppression effect of a bacterium belonging to the genus *Collimonas* on plant pathogenic bacteria was conducted.
<Prepared Samples>
Sample 1: 0.7 g of a Towada stone powder, to which 100 μL of a pre-culture liquid of D-25 strain was inoculated and 200 μL of sterilized water was added
Sample 2: 100 μL of a pre-culture liquid of D-25 strain, to which 900 μL of sterilized water was added
Sample 3: 0.7 g of an unsterilized Towada stone powder, to which 100 μL of a pre-culture liquid of D-25 strain was inoculated and 300 μL of sterilized water was added
Sample 4: 0.7 g of a sterilized Towada stone powder, to which 100 μL of a pre-culture liquid of D-25 strain was inoculated and 300 μL of sterilized water was added Experimental Method

*Collimonas* D-25 strain was pre-cultured under shaking in a 1/10 TSB culture medium for 4 days at 24° C. The number of the viable bacteria after the pre-culturing was $2.6 \times 10^7$ cfu/mL.

Each sample was prepared and subjected to static culturing at room temperature for 2 days, 3 mL of sterilized water was added to each sample, and the resultant was stirred by using vortex. For D-25 in the stirred culture liquid, the number of the viable bacteria was counted by using a 1/10 TSA culture medium.

Furthermore, a culture liquid of each sample was inoculated in 10 μL of TSA and 1/10 TSA culture medium, and an agar slice of *Rhizoctonia* was inoculated at the same time. The culturing was conducted at room temperature, and whether or not D-25 strain suppresses *Rhizoctonia* was observed.

(Results)
(1) Results of Count of Numbers of the Viable Bacteria

The results of the count of the numbers of the viable bacteria are shown in Table 11.

TABLE 11

|  | Sample 1 | Sample 2 | Sample 3 | Sample 4 |
|---|---|---|---|---|
| Number of viable bacteria (cfu/mL) | $1.1 \times 10^7$ | $2.1 \times 10^7$ | $2.1 \times 10^7$ | N.D. |

Since proliferation was also observed in Sample 2, it seems that it is appropriate to consider that the proliferation is caused by the nutrient contents that were brought by the 1/10 TSB in the pre-culturing rather than by the elution of the nutrient contents from the Towada stone.

(2) Suppression Effect on Plant Pathogenic Bacteria

When D-25 was cultured in Towada stone and the suppression effect on the plant pathogenic bacteria was confirmed, the blocking circles were formed more clearly than those in D-25 alone.

Furthermore, when an experiment of a suppression effect was conducted without a sterilization treatment of Towada stone, considerably large blocking circles were formed.

For the former case, it is assumed that, when Towada stone is added, a gene that reinforces the proliferation of microorganisms and the phagocytosis action of chitinase and the like is expressed by the effect of the minerals and the like in the Towada stone.

For the latter case, it was confirmed by visual observation that several kinds of bacteria and molds resided in Towada stone, and a matter that looked like the inhibition of the growth of fungal filaments was confirmed at the boundaries of the blocking circles. Therefore, the presence of a microorganism having a strong antibacterial activity was suggested.

INDUSTRIAL APPLICABILITY

This invention enables storage of bacteria belonging to the genus *Collimonas* for a long period of time, and thus the bacteria can be utilized as microorganism agrochemicals.

Furthermore, since it is also possible to use green tuff as a support, the bacteria can be utilized as coating materials for plant seeds.

The invention claimed is:

1. A method for storing bacteria belonging to the genus *Collimonas*, comprising:
    culturing bacteria belonging to the genus *Collimonas* in a culture medium containing a rice bran culture medium and/or a soy pulp culture medium, and green tuff as an additive in an amount suitable for the storage of bacteria belonging to the genus *Collimonas*; and
    storing said cultured bacteria belonging to the genus *Collimonas* under an ordinary temperature in a sealed state.

2. A method for storing bacteria belonging to the genus *Collimonas* according to claim 1, wherein the bacteria belonging to the genus *Collimonas* is cultured by adjusting a ratio of the weight of the green tuff to a water content in the culture medium liquid to be 7:3.

* * * * *